United States Patent [19]

Nelson et al.

[11] Patent Number: 4,918,244

[45] Date of Patent: Apr. 17, 1990

[54] PREPARATION OF MTBE FROM TBA AND METHANOL

[75] Inventors: Edward C. Nelson, Lagrangeville, N.Y.; David A. Storm, Montvale, N.J.; Mahendra S. Patel, Croton on Hudson, N.Y.

[73] Assignee: Texaco Inc., White Plains, N.Y.

[21] Appl. No.: 45,631

[22] Filed: May 4, 1987

[51] Int. Cl.$^4$ .............................................. C07C 41/09
[52] U.S. Cl. .................................................... 568/698
[58] Field of Search ........................................ 568/698

[56] References Cited

U.S. PATENT DOCUMENTS

| | | | |
|---|---|---|---|
| 2,282,469 | 5/1942 | Frolich | 568/698 |
| 3,928,483 | 12/1975 | Chang et al. | 568/698 |
| 4,232,177 | 11/1950 | Smith | 568/697 |
| 4,551,567 | 11/1985 | Smith | 568/698 |

Primary Examiner—Howard T. Mars
Attorney, Agent, or Firm—Robert A. Kulason; James J. O'Loughlin; Vincent A. Mallare

[57] ABSTRACT

A process for preparing MTBE wherein TBA and MeOH are continuously fed to a rectification tower having a packed solid-acid catalyst bed where the TBA and MeOH react in the presence of the catalyst to produce MTBE.

2 Claims, 2 Drawing Sheets

PROCESS FOR THE PRODUCTION OF MTBE

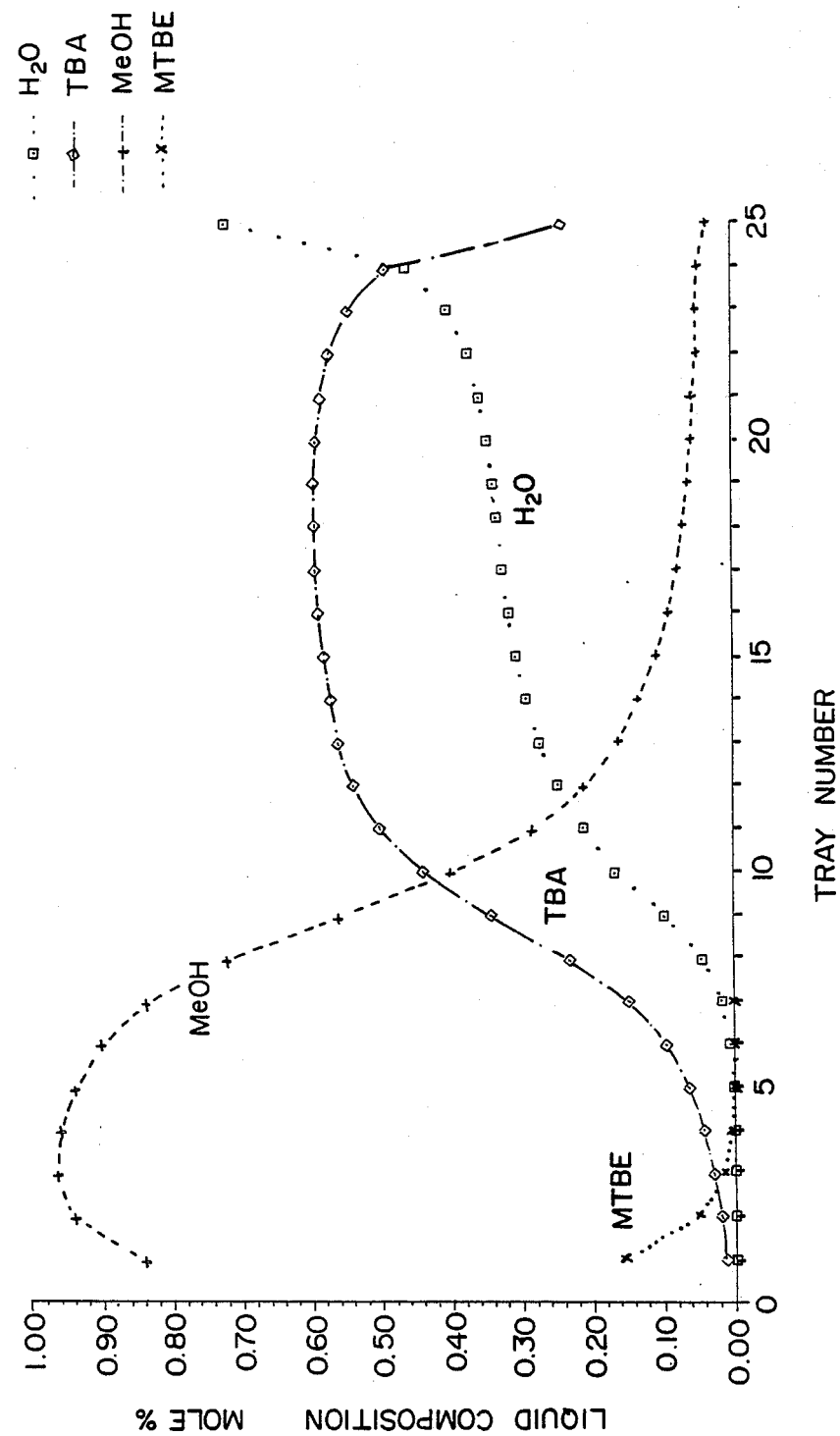

PREPARATION OF MTBE FROM TBA AND METHANOL

FIELD OF THE INVENTION

The present invention relates to a process for the preparation of tertiary-alkyl ethers and, more particularly, to the preparation of ethers such as methyl-t-butyl ether (MTBE) and t-amyl methyl ether (TAME).

BACKGROUND OF THE INVENTION

Recent concern with environmental pollution by lead from the exhaust gases of internal combustion engines has forced a transition away from the use of lead anti-knock compounds in gasoline. In order to produce unleaded gasoline having an acceptable octane value without varying the compounding ratio of gasoline, it has become necessary to use organic blending compounds with high octane ratings.

A variety of organic compounds are known as fuel extenders and octane value improving agents. Particularly, the well known organic compounds include methyl t-butyl ether (MTBE), ethyl t-butyl ether, isopropyl t-butyl ether, t-amyl methyl ether (TAME) and t-butyl alcohol (TBA). The preparation of these ethers and alcohols by the catalytic addition of an alcohol or water to an olefin having a double bond on a tertiary carbon atom has been extensively studied.

In the past and presently, there have been, and are, many processes developed, and being developed, to produce methyl t-butyl ether (MTBE). For the most part, these processes have involved several steps and have been comprehensive as well as being costly. The problem being that only a substantially pure product of MTBE is useful in fuels. Contaminated fuels are not effective and require further treatment to be useful in fuels.

Thus, it is an object of the present invention to provide an economical one-step process for producing a product of a substantially pure t-alkyl ether such as MTBE or TAME.

DISCLOSURE STATEMENT

U.S. Patent No. 2,480,940 discloses catalysts employed for the etherification or alcoholification of olefins which have been acids such as $H_2SO_4$, Lewis acids, platinum metal salts and various heterogenous catalysts, and discloses solid sulfonated organic resins that may be used for ion exchange applications.

U.S. Pat. No. 4,071,567 discloses a two-step process for preparing methyl t-butyl ether with methanol and isobutylene in the presence of an acid ion exchange resin.

U.S. Pat. 4,198,530 discloses a two-step process for preparing tertiary butyl methyl ether from isobutene and methanol in the presence of an acidic ion exchange catalyst.

SUMMARY OF THE INVENTION

The present invention provides a method of preparing methyl t-butyl ether (MTBE). The process comprises continuously feeding t-butyl alcohol (TBA) and methanol (MeOH) into a packed solid-acid catalyst bed, in a reactor-separator rectification column in the presence of the solid acid catalyst, whereby a product of substantially pure MTBE is separated from the reaction mixture.

The process is carried out at a temperature of about 5.0 to about 250° C., under a pressure of between about 0.25 and about 25 atmospheres.

DETAILED DESCRIPTION OF THE INVENTION

Figure 1:
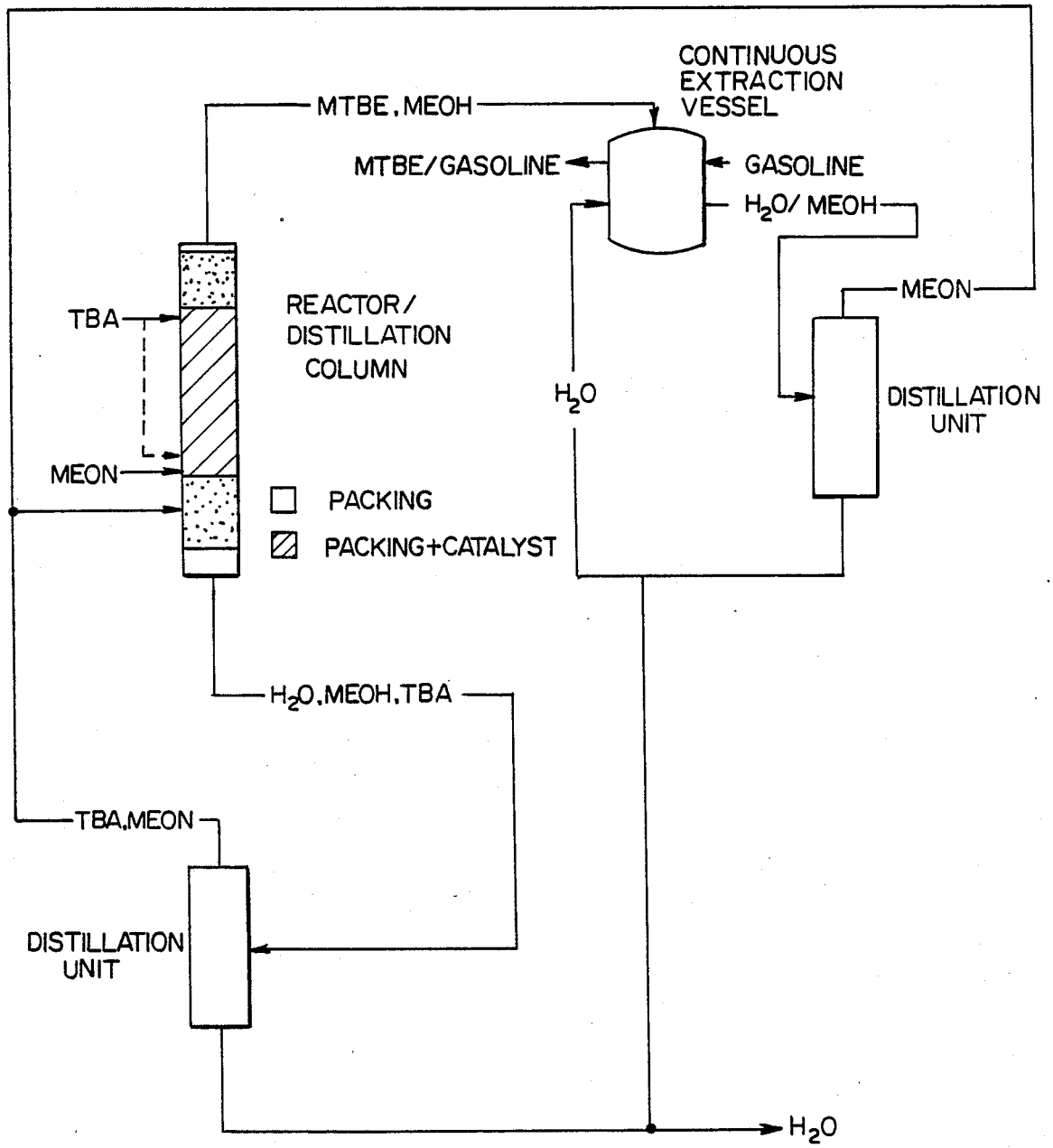

Although the invention will be described with specific reference to the preparation of methyl t-butyl ether (MTBE) for the purpose of clarity, it should be understood that other ethers and alcohols prepared by the catalytic addition of alcohol or water to olefins having a double bond at the tertiary carbon are within the scope of the present invention. Such olefins include isobutylene, 2-methyl butene-1, 2 methyl butene-2, 2-methyl pentene-1 and 2-methyl pentene-2.

The process that may be used for preparing MTBE according to the present invention is illustrated by the following equation:

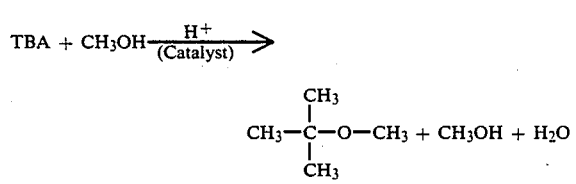

Tertiary alkyl ethers, such as methyl t-butyl ether (MTBE) and t-amyl methyl ether (TAME) are useful as fuel extenders and, in particular, as gasoline octane enhancers. Generally, processes for producing these materials all rely on a primary alcohol and an olefin which contains a double-bond on a tertiary carbon as raw materials. The reactions are carried out in the liquid phase and in the presence of Lewis acids, mineral acids or organic acids. Ion exchange resins in their acid form are particularly suitable for this reaction.

The optimum results are obtained when macroreticular resins are used such as the Amberlyst 15 type. The catalyst, i.e., a solid-acid catalyst, may be selected from the group of materials consisting of Amberlyst 15 and related compositions, Nafion-H resins and related compositions, $SiO_2/Al_2O_3$, $Al_2O_3/B_2O_3$, hydrogen montmorillonite and kaolinite, metal sulfates, heteropolyacids, zeolites, iron silicates, alumina phosphates and alumina-silica phosphates.

The catalyst is packed in a rectification tower and is substantially insoluble to the liquid components therein. The catalyst can be present in the column either undiluted or with an inert diluent in weight ratios of as little as 200/1 inert to catalyst.

The process of the present invention and a condensation phase of the components of the process (i.e., MTBE, MeOH, TBA and $H_2O$) are illustrated in the attached drawings which are FIG. 1 is a flow diagram of the present process showing the equipment used therein; and FIG. 2 is a graph illustrating a calculation of the condensed phase of the components in the present process.

In the present process, TBA is used to produce MTBE. TBA is produced in large quantities from processes for producing propylene oxide from propylene. The subject of the present invention is a one-step process which makes it possible to achieve high conversions of TBA and MeOH to MTBE using a distillation column as the reactor and primary separator.

An object of the present invention is to obtain a product stream which is substantially MTBE and substantially free of water, TBA and MeOH. This can be accomplished by catalytic distillation in a distillation column that has been packed with acidic packing material. Under these conditions, low-boiling MTBE is removed at the top of the reaction/ distillation column and by-product water is removed at the bottom of the column. Adding TBA near the top of the column, and methanol near the bottom of the column, results in a dual mass action effect. Near the bottom of the column, where methanol is in excess, the conversion of TBA to MTBE is nearly complete and not any TBA is present in the bottoms. Near the top of the column where TBA is in excess, the conversion of MeOH to MTBE is complete and no methanol is present in the overhead. Above the point at which TBA enters the column, the distillation trays contain only TBA and MTBE which can be easily separated in ascending trays. Below the point at which methanol is added, the distillation trays contain only water and methanol which can be easily separated in descending trays.

As shown in FIG. 1, TBA and MeOH are continuously fed, i.e., pumped, into the rectification column. TBA and MeOH are fed continuously in a molar ratio of TBA to MeOH of between about 10:1 and about 1:10. The point of entry of either TBA or MeOH can be varied to provide the maximum conversion of TBA and MeOH and maximum productivity of MTBE. In the present process, the adding of a stream of TBA into the top of the packed catalyst bed improves the productivity of the rectification column three-fold. The temperature profile of the column can be controlled by the boil-up from the reactor or by the application of external heat or by a combination of both methods. Because the reaction between TBA and MeOH is endothermic, the application of external heat to the rectification column is desirable in maintaining the temperature profile of the column and the rate of the reaction. The MTBE can be purified of any residual methanol by partitioning between gasoline and water. The MTBE-gasoline fraction can be used as a high-octane blending component. The aqueous extracts are separated by distillation; water is recycled to the extractor and methanol is recycled to the rectification column. Alternatively, the MTBE can be purified by a conventional distillation under pressure. The bottoms from the rectification column consist predominantly of $H_2O$, MeOH and some TBA. These components can be separated by distillation, the water discarded and the TBA and methanol recycled to extinction.

The process of using a rectification column as a reactor has been known and described in the literature. There is described a process for preparing MTBE by reacting a mixture of methanol and isobutylene over an acidic catalyst in a rectification column. The process described herein differs substantially from the process of the literature and offers several key and unexpected advantages including:

1. The reaction of either isobutylene or TBA with methanol takes place in a condensed, liquid phase on the surface of the catalyst. Using isobutylene as a reactant limits the rate of the reaction because of the limited solubility of isobutylene in the condensed phase. In contrast, TBA coexists with methanol as a completely miscible condensed phase at reaction conditions and is therefore in high concentration in the liquid film around the catalyst particle.

2. A second advantage of using TBA rather than isobutylene is that TBA can assume a temperature driven concentration profile alone the reactor/distillation column. In one embodiment of the present invention, the rate of mass transfer within the column is much greater than the rate of reaction. In this mode of operation, the composition in each tray is similar to that found in an ordinary fractional distillation of a mixture of MTBE, MeOH, TBA and water. In accord with these assumptions, a calculation of the condensed phase was made by a computer simulation (SIMSI) and is graphically displayed in FIG. 2.

Since the reaction of TBA and methanol is thermodynamically controlled, increasing the amount of methanol present in a particular tray of the column should increase the conversion of TBA in that tray. For example, tray No. 8 contains a ratio of TBA to MeOH of 1:3 while tray No. 6 contains a TBA to MeOH ratio of 1:9. Thus, the conversion of TBA to MTBE should increase in ascending trays. To confirm this speculation, a 1:1 TBA/MeOH mix (Example 3 below) and a 1:9 mix of TBA/MeOH was treated with Amberlyst 15 resin. At equilibrium the conversions of TBA to MTBE were 48 and 86 percent respectively. In contrast, isobutylene is a gas at reaction conditions thus, no concentration profile is possible.

3. The reaction of TBA and MeOH produces both MTBE and water. Therefore, removing water as well as MTBE from each tray of the distillation should improve the equilibrium conversion of TBA. Again, the computer simulation shows that the concentration of water diminishes moving up the column. The net effect would be to increase the conversion of TBA to MTBE in successive trays. In contrast, isobutylene and MeOH do not react to form a sideproduct.

The results obtained using a distillation column as the reactor and separator were compared with those obtained using the same catalyst in a batch reactor. It was found that the selectivity to MTBE was essentially the same (i.e., 71% vs 72%) but the conversion of TBA was improved from 71 to 95 percent and the yield of MTBE was improved from 51.2 to 66 percent. In addition, the product obtained from the distillation reactor contained no TBA or water, whereas the product obtained from the batch reactor contained 12.6 wt. % TBA and 8.2 wt. % $H_2O$.

According to the present invention, it was also demonstrated that MTBE containing methanol can be separated by partitioning the MeOH and MTBE between an aqueous and an organic layer. A mixture of gasoline and a typical azeotropic composition of MTBE and MeOH was prepared. It was found that an aqueous extraction of such a mixture resulted in the complete separation of methanol from the organic phase, producing a blending component containing 28.8 percent MTBE.

The advantages of the present invention are more evident when considering the following examples:

EXAMPLE 1

The process was performed in a conventional fractional distillation apparatus open to the atmosphere through a dry-ice acetone trap. A Hempel column, approximately 1 inch in diameter, was packed with a physical mixture of glass beads (210 g) and Amberlyst 15 resin beads (5 g), 44.5 g of methanol and 34.8 g of t-butyl alcohol was refluxed up into the column and an azeotrope of methanol and MTBE was collected from the outlet of the column. The composition of the distillate by weight was 67.7 percent MTBE, 23.0 percent MeOH and 9.3 percent isobutene. The distillation was continued until 95 percent of the original TBA had been converted to products. The final composition of the pot by weight was 38 percent water, 55.3 percent methanol and 6.7 percent TBA. The material remaining in the rectification column at the end of the experiment was 95 percent methanol and less than 5 percent water and TBA. The productivity overall was 0.42 g MTBE/g resin-hr, declining from 0.47 to 0.32 as the pot concentration of water increased and TBA decreased. The selectivity to MTBE was 70 percent and the yield was 66 percent. The only other side-product obtained was isobutene.

EXAMPLE 2

A 250 ml flask was fitted with an efficient condenser and connected thru a dry-ice acetone trap to the atmosphere. The reactor was charged with 44.5 g of methanol, 34.8 g of TBA and 5 g of Amberlyst 15 resin. The mixture was refluxed for 7.13 hours, at which time an equilibrium mixture of TBA, MeOH, MTBE and water was present. The composition of the mixture by weight was 26.7 percent MTBE, 12.65 percent TBA, 52.5 percent MeOH and 8.2 percent water. The calculated productivity was 0.59 g MTBE/g resin/h, the selectivity to MTBE was 72 percent and the conversion of TBA was 71 percent. The yield of MTBE was 51.2 percent. The only other side-product obtained was isobutene. EXAMPLE 3

25 g of either a 1:1 (by weight) or 1:9 mixture of TBA and MeOH were charged to a pressure tube with 2 g of dry Amberlyst 15 resin. The vessel was sealed and magnetically stirred at 60C in an oil bath for 5 hours. The vessel was quickly cooled to room temperature and examined by GLC. Conversions of TBA to MTBE of 48 mol. % and 85 mol. % were determined for the 1:1 and 1:9 mixtures, respectively

EXAMPLE 4

22.0 g of MTBE, 18.5 g of TBA, 4.5 g of H2O and 24 g of MeOH was fractionally distilled at atmospheric pressure through a packed column containing 200 g of 6 mm glass beads. 15 g of distillate boiling between 49 and 51° C. was collected. Analysis by GLC on Porapak Q column (⅛"×6' stainless steel) revealed that the composition of the distillate was 86 wt. % MTBE and 14 wt. % MeOH. 86 g of MTBE and 14 g of MeOH were blended with 200 g of unleaded base fuel. 100 g of the mixture was extracted with 50 ml portions of water. After one extraction, the mass balance of the aqueous and organic phases was 98.9 wt. % of theoretical; the aqueous fraction contained 98 wt. % of the original MeOH and 3.0 percent of the original MTBE. After three (3) extractions, the mass balance was 99.1 wt. % and the aqueous fractions contained 100 percent of the methanol and 6 percent of the MTBE present in the original mixture The final composition of the organic fraction was 28.8 percent MTBE in gasoline; no MeOH was present as judged by GLC analysis on a Porapak Q column.

EXAMPLE 5

The apparatus used in Example 1 was modified by adding a feed line through the top of the reactor which was used for introducing TBA directly into the catalyst bed of the reactor. 44.5 g of methanol and 34.8 g of t-butyl alcohol were refluxed up into the column and an azeotrope of methanol and MTBE was collected from the outlet of the column. Analysis of a sample of the distillate revealed an average productivity of 0.25 g MTBE/g resin/hr The TBA feed pump was then started at 0.60 mL/min and an immediate rise in the column temperature was noted. After 30 minutes, a sample of the distillate was obtained and a productivity of 0.72 g MTBE/g resin/hr was calculated.

The present invention as described above may be modified in many ways by those of ordinary skill in the art without departing from the scope of the invention as set forth in the appending claims.

We claim:

1. A one step continuous process for preparing MTBE comprising continuously feeding TBA and MeOH in a molar ratio of TBA to MeOH of between about 10:1 and about 1:10 into a packed solid-acid catalyst bed of Amberlyst 15 catalyst in a reactor-separator rectification column, said TBA being reacted with MeOH in the presence of said solid acid catalyst. wherein said TBA is fed to the top of said catalyst bed and said MeOH is fed into the bottom of said catalyst bed to provide a complete conversion of these components to substantially pure MTBE from the top of said rectification column.

2. The process of claim 1, wherein the process is carried out at a temperature ranging from about 5.0° to about 250° C., under a pressure of between about 0.25 and 25 atmospheres.

* * * * *